(12) United States Patent
Kurozumi et al.

(10) Patent No.: US 7,230,698 B2
(45) Date of Patent: Jun. 12, 2007

(54) PARTICLE SIZE DISTRIBUTION MEASUREMENT DEVICE

(75) Inventors: Takuji Kurozumi, Kyoto (JP); Yoshiaki Togawa, Kyoto (JP)

(73) Assignee: Horiba, Ltd., Kyoto (JP)

( * ) Notice: Subject to any disclaimer, the term of this patent is extended or adjusted under 35 U.S.C. 154(b) by 109 days.

(21) Appl. No.: 11/213,358

(22) Filed: Aug. 26, 2005

(65) Prior Publication Data

US 2006/0050279 A1 Mar. 9, 2006

(30) Foreign Application Priority Data

Aug. 30, 2004 (JP) ............................ P2004-249729
Aug. 30, 2004 (JP) ............................ P2004-249730

(51) Int. Cl.
*G01N 21/51* (2006.01)

(52) U.S. Cl. ..................................... 356/336

(58) Field of Classification Search .................... None
See application file for complete search history.

(56) References Cited

U.S. PATENT DOCUMENTS 5,632,890 A * 5/1997 Sugimoto ................ 210/67.11
6,001,244 A * 12/1999 Salter et al. ................ 210/104

FOREIGN PATENT DOCUMENTS

JP 2000-155088 6/2000

* cited by examiner

*Primary Examiner*—Tu T. Nguyen

(57) ABSTRACT

In order to supply a dispersion medium to a circulation channel not accompanying any mingling of air and to accomplish the reduction of preparation time and the improvement of the measurement accuracy; a dispersion medium supply system 3 is connected in the vicinity of a drainage outlet 14 of a circulation channel 13 comprising a suspension circulation system 1 to pressure-pour a dispersion 3a from the dispersion medium supply system 3 to the circulation channel 13.

13 Claims, 10 Drawing Sheets

PARTICLE SIZE DISTRIBUTION MEASUREMENT DEVICE

BACKGROUND OF THE INVENTION

1. Field of the Invention

The present invention relates to a particle size distribution measurement device to measure the particle size distribution of particles distributed within the dispersion medium.

2. Description of Related Art

The technology to measure particle size distribution is essential to determine and evaluate the performance of particulate matters throughout wide areas, such as drugs, food, ceramics, cosmetics, paint and coloring matter, and the importance has increased as time goes by. As a method to measure the particle size distribution of particulate matters, a laser diffraction/scattering particle size distribution measurement device already exists. For example, in the laser diffraction/scattering particle size distribution measurement device disclosed in Japanese Laid-Open Patent Application 2000-155088, sample particles are distributed and dispersed in a dispersion medium as a suspension, and this suspension is supplied to a flow cell; a laser beam is irradiated to the flow cell in a state where the suspension is in the flow cell. The laser beam diffracted and/or scattered by the particles in the suspension is detected by a detector, and the intensity of the obtained diffracted light and/or scattered light is processed based upon the Fraunhofer Diffraction Theory and the Mie Scattering Theory; and the particle diameter of the sample is obtained.

To supply this suspension to the flow cell, a circulation channel to circulate the suspension is established, and a circulation bath, where a sample is dispersed in a dispersion medium, and a circulation pump intervene in this circulation channel, and it is designed so that a dispersion medium sucked from a dispersion medium tank via a dispersion medium supply system is poured into the circulation bath.

However, in the related conventional dispersion medium supply system, since a pouring end is established in the upper position of the circulation bath and is designed to discharge the dispersion medium from the pouring end and to pour it into the circulation bath, there is the defect that a portion of air existing within the circulation channel is pushed deeper at the time of initial pouring, and that falling causes the mingling of the air at the time of supply, so that in either case, air easily remains within the circulation channel after pouring the dispersion medium. If air ventilation processing is sufficiently performed after pouring in order to cope with these defects, there is another problem of extending the preparation time, and it is also highly possible that even with air ventilation processing, bubbles may remain within the circulation channel, and the generation of unnecessarily scattering light by the bubbles causes a reduction of the S/N ratio.

Further, a water level sensor to detect a filled level and a shortage level is established in the circulation bath to prevent overflow and an abnormal shortage of the suspension. Therefore, the design secures pouring of the dispersion medium and appropriate circulation of the suspension. In order to appropriately obtain the particle diameter of a sample, it is important to accurately control the concentration of the suspension.

The above-mentioned Japanese Laid-Open Patent Application 2000-155088, to adjust the concentration of the suspension, ah inspection light is irradiated to a flow cell while the suspension is circulated within a circulation channel, and the concentration is determined based on the ratio between the quantity of the inspection light from a light source and the quantity of the transmitted light, in other words, based upon transmittance, and, for example, if it is determined that the concentration is high, it is designed to conduct the following procedure while repeating drainage and filling.

The suspension is drained by an appropriate amount from the circulation channel, and then the dispersion medium is supplied via the dispersion supply system until the water level sensor detects the filled level in the circulation bath. The suspension is then again circulated within the circulation channel in the filled state; and the concentration is determined according to the irradiation of the inspection light, making it difficult to adjust by delicate pouring, so accurate adjustment of the concentration is difficult. By the same token, there is the problem that high accuracy of measurement and reproducibility for the measurement of the particle size distribution cannot be obtained.

SUMMARY OF THE INVENTION

The present invention has been accomplished with due regard to these problems. First, it is designed to supply a dispersion medium into a circulation channel not accompanying the mingling of air, and second, a circulation structure that becomes useful for the purpose of automatically adjusting the concentration of the particles in the dispersion medium efficiently is constructed, resulting in the resolution of the air residue problem and the concentration adjustment problem. By the same token, the primary objective of the present invention is to provide a particle size distribution measurement device that has high measurement accuracy and reproducibility.

In other words, the present invention is characterized by the fact that in a particle size distribution measurement device equipped with the general configuration of this type of particle size distribution measurement device, a dispersion supply system is connected in the vicinity of a drainage outlet of a circulation channel that composes a suspension circulation system, to pressure pour a dispersion medium into the circulation channel from the dispersion supply system.

Since it is usual for the drainage outlet to be arranged at a lower position of the circulation channel in this construction, pouring a dispersion medium into this section has the effect of forcing air out. Because new mingling of peripheral air is also avoided, air ventilation processing is basically unnecessary with the present invention.

As a specific embodiment, a particle size distribution measurement device can be provided where the above-mentioned drainage outlet is established in a pipe line at the lowest position of the circulation channel, and the dispersion supply system is connected to the upper course of the drainage outlet in this pipe line.

In order to prevent circulating particles from mingling with pour piping without lowering measurement accuracy, it is preferable to construct it to selectively connect the dispersion supply system to the suspension circulation system via the opening/closing motion of a valve body, and to arrange the internal end of the valve body at the closed position to be roughly smooth without any unevenness or steps relative to the internal surface of the pipe line in the circulation channel on that occasion.

In order to additionally reduce the possibility of air residue and to simultaneously simplify the structure and to reduce the cost, it is desirable to assemble the suspension drainage system, the suspension supply system and the circulation channel as a unit using a single chassis.

Further, in a particle size distribution measurement device equipped with the general configuration of this type of particle size distribution measurement device, the present invention is characterized by being equipped with a liquid level detecting means to detect the liquid level of the suspension in the circulation bath at least at multiple points; and a control means to control pouring the dispersion medium and/or the drainage of the above mentioned suspension based upon the detection signal of this liquid level detecting means.

Since an intermediate liquid level can be detected in this configuration, it becomes possible to more accurately adjust the liquid level of a circulation bath, useful for the concentration adjustment of a suspension by more strictly controlling pouring of the dispersion medium and the drainage of the suspension.

The liquid level detecting means can also be constructed with multiple liquid level sensors, and constructed with a single multipoint detectable liquid level sensor or continuous detectable liquid level sensor.

As a specific embodiment of the liquid level detecting means, one that is capable of detecting the filled level and the shortage level and one point or multiple points in between the filled level and the shortage level, and another one that is able to intermittently or continuously detect the liquid level within a pre-determined range from the filled level to the shortage level can be provided.

In order for the concentration of the suspension to be automatically adjustable, it is desirable that the above-mentioned control means be equipped with a concentration information acquisition part that acquires information regarding the concentration of the particles contained in the suspension according to transmittance of an inspection light; a 1st determination part that determines whether or not the concentration of the particles contained in the suspension is a pre-determined concentration based upon the acquired concentration information; a 1st calculator that calculates the required amount of the dispersion medium to be poured if it is determined that the concentration is higher by this 1st determination part; and a driver that drives instruments required for pouring the dispersion medium based upon the calculated value by the above-mentioned 1st calculator.

In order for the concentration of the suspension to be automatically adjustable without being restricted by the volume of the circulation bath, it is desirable that the control means be equipped with a concentration information acquisition part that acquires information regarding the concentration of the particles contained in the suspension according to transmittance of an inspection light; a 1st determination part that determines whether or not the concentration of the particles contained in the suspension is the pre-determined concentration based upon the acquired concentration information; a 1st calculator that calculates the required amount of the dispersion medium to be poured if it is determined by the 1st determination part that the concentration is higher; a 2nd determination part that determines whether or not the circulation bath will be filled due to pouring according to the above-mentioned amount to be poured and the liquid level detected by the above-mentioned liquid level detecting means; a 2nd calculator that calculates the required amount of the suspension to be drained and the required amount of the dispersion medium to be poured if it is determined that the circulation bath will be filled due to pouring; and a driver that drives instruments required for pouring the dispersion medium and/or the drainage of the suspension based upon the calculated value(s) by the above-mentioned 1st calculator and/or 2nd calculator.

In these configurations, it is appropriate that the control means be additionally equipped with a request part that requests adding more particles if it is determined by the 1st determination part that the concentration be lower.

DETAILED DESCRIPTION OF THE PREFERRED EMBODIMENTS

An embodiment of the present invention is described hereafter, with reference to the drawings.

Figure 1:
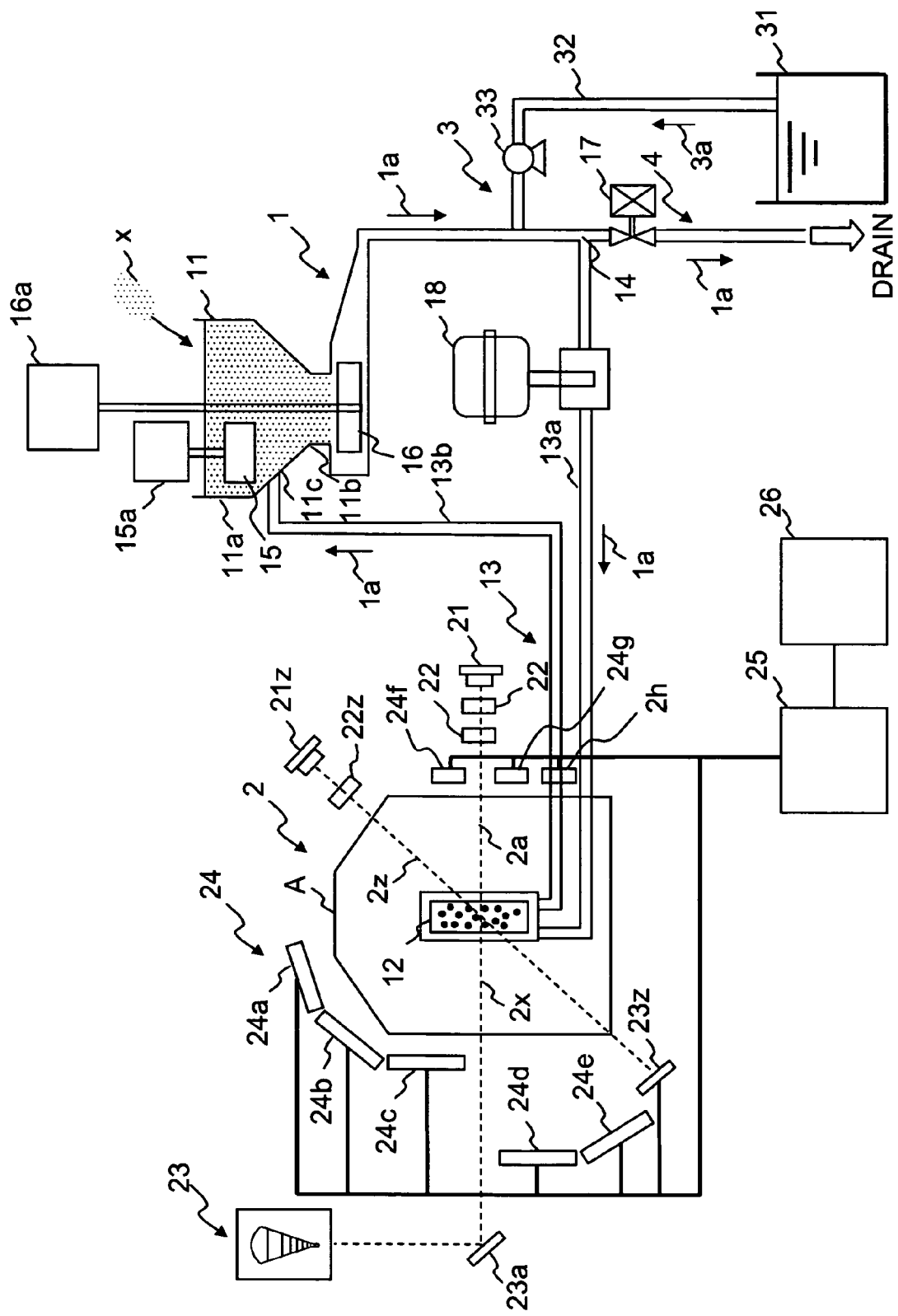
FIG. 1 is a system diagram that shows an outline of the particle size distribution measurement device relating to an embodiment of the present invention.

FIG. 1 is a schematic view that shows the configuration of the light scattering particle size distribution measurement device relating to an embodiment of the present invention. This particle size distribution measurement device comprises a suspension circulation system 1 where a circulation bath 11 and a flow cell 12 are connected via a circulation channel 13 so as to circulate a suspension 1a where sample particles x are dispersed in a dispersion medium 3a; an optical measurement system 2 where a laser beam 2a, which is an inspection light, is irradiated onto the suspension 1a that flows within the above-mentioned flow cell 12, and the particle size distribution of the sample particles x in the above-mentioned suspension 1a is measured based upon its diffracted light and/or scattered light; a dispersion medium supply system 3 that supplies the dispersion medium 3a to the above-mentioned suspension circulation system 1; and a suspension drainage system 4 that drains the suspension 1a from a drainage outlet 14 established at a portion of the above-mentioned circulation channel 13.

In the above-mentioned suspension circulation system 1, the sample particles x (or slurry) to be poured and the dispersion medium 3a (for example, purified water or alcohol) that disperses this sample x are mixed and the suspension 1a is formed in the circulation bath 11, and a stirring wing 15, which is drivable by a stirring motor 15a, is immersed in an intermediate liquid bath 11c situated between an upper liquid bath 11a and a lower liquid bath 11b. Concurrently, a centrifuge type circulation pump 16, which also has a role as a drainage pump, is liquid-tightly attached to the bottom of the circulation bath 11, and becomes drivable by a circulation motor 16a. A float type a liquid level detecting means 10 (refer to FIG. 2) for the purpose of detecting the liquid level of the suspension 1a is arranged within the circulation bath 11. An outlet of the above-mentioned circulation pump 16 accompanying the circulation bath 11 is connected to the flow cell 12 via outward piping 13a that comprises one section of the circulation channel 13, and another outlet of the flow cell 12 is connected to the above-mentioned circulation bath 11 via homeward piping 13b that composes the other section of the circulation channel 13.

The flow cell 12 is arranged within a sample chamber A, and is designed so that the suspension 1a provided from the outside is liquid-tightly circulated between a pair of transparent plates with transmittance and the suspension 1a can be led to the outside, and the laser beam 2a is irradiated onto the transparent plates.

The outward piping 13a has an ultrasound oscillator 18 halfway, which generates ultrasound, preventing the cohesion of the particles in the suspension 1a going toward the flow cell 12.

The homeward piping 13b is connected to the intermediate liquid bath 11c within the circulation bath 11 so as to reflow the suspension 1a after being circulated into the circulation bath 11.

In the meantime, in the above-mentioned optical measurement system 2, as shown in FIG. 1, a laser light source 21, projection lenses 22, a narrow-angle scattered light detector 23 and a wide-angle scattered light detector 24 are arranged to surround the sample chamber housing the flow cell 12. Concurrently, it is provided with a signal processor 25, which processes signals transmitted from the narrow-angle scattering detector 23 and the wide-angle scattered light detector 24, and an arithmetic processor 26.

The laser light source 21 is arranged at the facing position of the flow cell 12, and emits the parallel laser beam 2a. The projection lenses 22 are arranged between the laser light source 21 and the flow cell 12, and appropriately condense the laser beam 2a emitted from the laser light source 21 and irradiate it onto the suspension 1a within the flow cell 12.

The narrow-angle scattered light detector 23 is arranged in a position so as not to directly face the flow cell 12; in other words, in a position where the laser beam 2a, which transmits through the flow cell 12 and is bent by a movable mirror 23a, is condensed and focused. This narrow-angle scattered light detector 23 is a detector where multiple photosensors that have a ring-state or semi-ring-state acceptance surface, the radius of which respectively differs from each other, are concentrically arranged using the optical axis of the projection lenses 22 as a center, and among the diffracted and/or scattered focused laser beams 2x by the particles within the flow cell 12, a light scattered/diffracted at a comparatively small angle is received per scattering angle, respectively, and their light intensities are measured. In other words, the photosensors arranged around the external circumference side relatively receive light at a larger scattering angle, and the other photosensors arranged around the internal circumference side receive light at a smaller scattering angle. In general, the smaller the particle diameter becomes, the more greatly the light scatters, so the light intensity detected by the photosensors arranged around the external circumference side reflects the quantity of particles with a smaller particle diameter, and the light intensity detected by the photosensors arranged around the internal circumference side reflects the quantity of particles having a greater particle diameter.

The wide-angle scattered light detector 24 is arranged around the periphery of the flow cell 12, and individually detects light that has been scattered/diffracted at a comparatively greater angle among the focused laser beam 2x, which has been diffracted or scattered by the particles with a smaller particle diameter within the flow cell 12 per scattering angle. Specifically, this wide-angle scattered light detector 24 is composed of multiple photosensors 24a through 24h, arranged in a position where the laser beam 2x, which scatters at a different angle from that of the focused laser beam 2x entering into the narrow-angle scattered light detector 23, can be received, respectively, and the scattered light due to the particles within the flow cell 12 is detected per scattering angle according to each arranged angle. The photosensors 24a through 24e detect the front scattering light and the photosensors 24f through 24h detect the rear scattering light, respectively.

The signal processor 25 sequentially receives signals transmitted from the narrow-angle scattered light detectors 23 and photosensors 24a through 24h; A/D-converts them; and enters the converted signals into the arithmetic processor 26.

Figure 3:
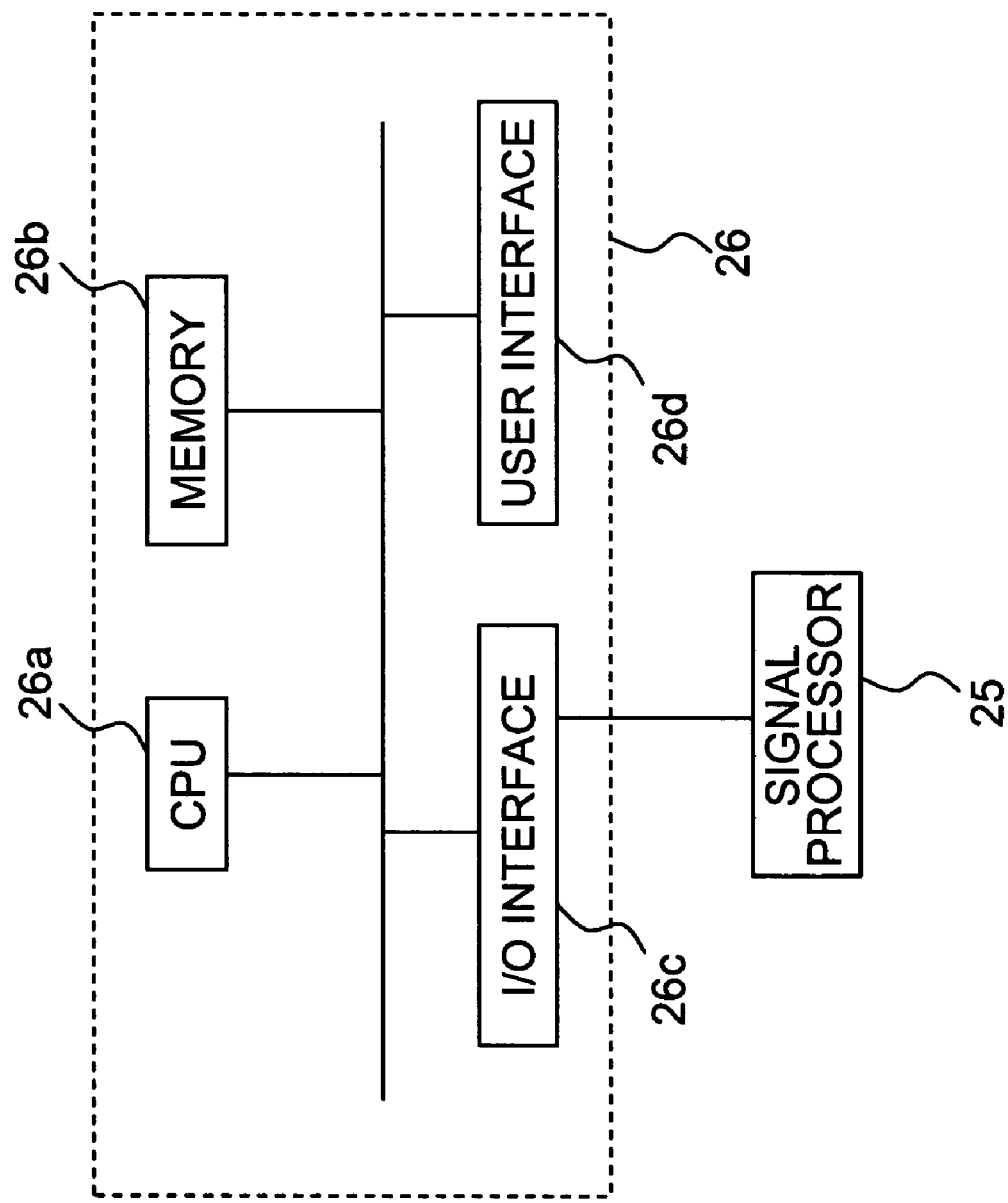
FIG. 3 is a function explanatory diagram of the arithmetic processor used in the embodiment.

The arithmetic processor 26 is a processor where the function of a versatile computer is utilized in this embodiment, and as shown in FIG. 3, is equipped with a CPU 26a, a memory 26b, an I/O interface 26c and a user interface 26d, and a program for obtaining the particle size distribution in the particle group by processing the output (digital data concerning the light intensity), which has been converted into a digital signal, from the narrow-angle scattered light detector 23 and the photosensors 24a through 24h, based upon the Fraunhofer Diffraction Theory and the Mie Scattering Theory, and another program for the purpose of a concentration check based upon the quantity of a transmitted light and the quantity of an irradiated light are stored. The CPU 26a appropriately reads out the programs and performs a pre-determined operation and/or processing; and stores the operational results in a memory 26b, or displays the operational results on a display comprising a section of the user interface 26d. In the present embodiment, the detection of a diffracted light or a scattered light within a wide range enables obtaining particle size distribution in the particle group in a wide range extending from a comparatively large particle diameter to a minute particle diameter.

In order to secure a wider measurement range from large particles to minute particles, not only the above-mentioned laser beam 2a but an LED beam 2z with a different wavelength as shown in FIG. 1 can be simultaneously used. For this purpose, an LED light source 21z, a projection lens 22z and a photo detector 23z that respectively correspond to the above-mentioned laser light source 21, the projection lenses 22 and the narrow-angle scattered light detector 23 are established in the device. The above-mentioned photosensors 24d and 24e are also used for receiving the scattering light of this LED light 2z.

On the other hand, the above-mentioned dispersion medium supply system 3 is equipped with a dispersion medium tank 31; dispersion medium supply piping 32 where one end is immersed into this dispersion medium tank 31 and the other end is connected to the above-mentioned suspension circulation system 1; and a pour pump 33 that intervenes within this dispersion medium supply piping 32, and is designed to that the drive of the pour pump 33 results in sucking the dispersion medium 3a from the dispersion medium tank 31 and the supply to the suspension circulation system 1.

The suspension drainage system 4 is connected to the circulation channel 13, comprising the above-mentioned suspension circulation system 1, via an electromagnetic directional control valve 17, and, the closed position of the directional control valve 17 causes the separation of the suspension drainage system 4 from the circulation channel 13, and the opened position of the directional control valve 17 causes the connection of one end of the suspension drainage system 4 to the circulation channel 13 and the suspension 1a within the circulation channel 13 is drained to a drain positioned at the other end, said direction control valve 17 being switched and driven by a solenoid.

The operation of the particle size distribution measurement device is described next. First, sample particles x are poured into the circulation bath 11. Next, the pour pump 33 in the dispersion medium supply system 3 is started, and the supply (pouring) of the dispersion medium 3a is started into the circulation bath 11. At this time, the directional control valve 17 is set to the circulation mode.

When a pre-determined quantity of the dispersion medium 3a is supplied into the circulation bath 11 and throughout the circulation channel 13, the supply pump 33 of the dispersion medium supply system 3 stops based upon an output signal of the liquid level detecting means 10, and the supply of the dispersion medium 3a is stopped.

Subsequently, the operation to start dispersion processing triggers the start of the circulation motor 16a, and the circulation pump 16 starts operating. Concurrently, the ultrasound oscillator 18 starts operating. Due to this, the following circulation is repeated: the suspension 1a where the sample particles x is dispersed flows from the inside of the circulation bath 11 to the circulation channel 13. In the meantime, the suspension 1a passes through the flow cell 12 and returns to the circulation bath 11.

The concentration of the obtained suspension 1a is checked due to the irradiation of the laser beam 2a from the laser light source 21 in the measurement system 2 toward the flow cell 12 in a state in which the suspension 1a circulates within the circulation channel 13 based upon the ratio between the quantity of light from the light source at that time and the quantity of the transmitted light detected in the center by the narrow-angle scattered light detector 23; in other words, based upon transmittance. As mentioned above, the program for the concentration check is stored in the memory 26b, and the CPU 26a reads out the program associated with the start of the operation for the dispersion processing and executes the program. If the concentration of the suspension 1a is not pre-determined, the concentration is checked again after dilution by the supply of the dispersion medium 3a or the concentration by the addition of the sample particles x, and when the concentration of the suspension 1a flowing into the flow cell 12 becomes appropriate for measurement, particle size distribution measurement is conducted. If the circulation bath 11 is already filled with the suspension 1a or it may become filled due to supply, the suspension 1a is drained via the suspension drainage system 4 prior to the supply.

Practically, for adjustment of concentration of the suspension 1a to the pre-determined concentration, it is desirable that the dispersion medium 3a first poured into the circulation bath 11 are adjusted to minimum quantity, and after that the dispersion medium 3a is gradually added. If too much dispersion medium 3a is poured first, drainage of the suspension 1a becomes necessary in the middle of the adjustment and the sample particles x are also drained wastefully.

In the above-mentioned construction, the present embodiment is characterized by the fact that the dispersion medium supply system 3 is connected in the vicinity of the drainage outlet 14 of the circulation channel 13 comprising the above mentioned suspension circulation system 1 so as to pressure pour the dispersion medium 3a from the dispersion medium supply system 3 to the circulation channel 13.

Figure 2:
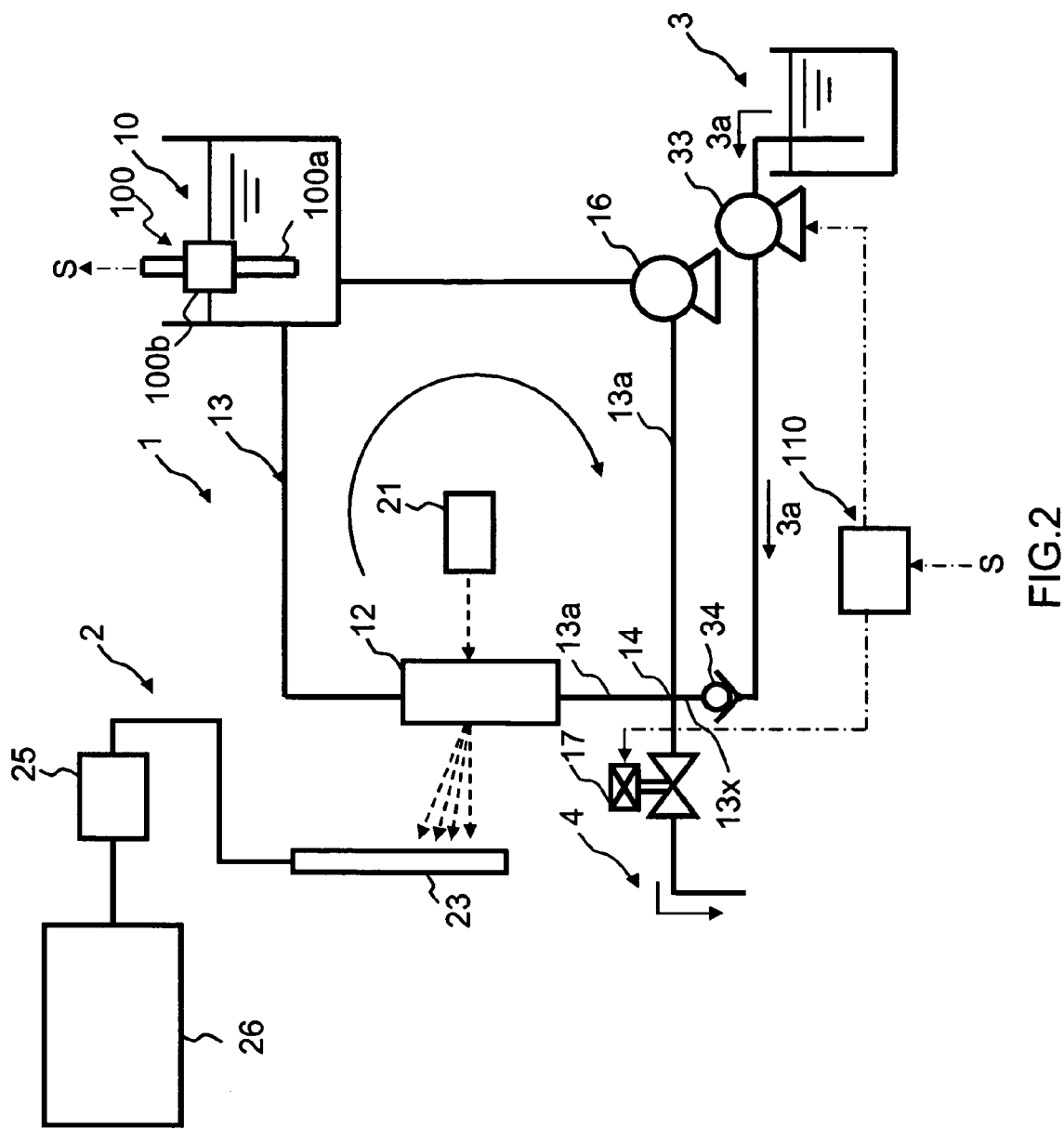
FIG. 2 is a diagram that clearly shows the connection sections of the dispersion medium supply system in the embodiment.

Specifically, in the present embodiment, the above-mentioned drainage outlet 14, as shown in FIG. 2, is opened at the pipe line at the lowest position of the circulation channel 13; in other words, at the pipe line in the middle of the outward piping 13a, and, the dispersion medium supply piping 32 comprising the dispersion medium supply system 3 is connected to an upper course 13x of the drainage outlet in the pipe line. In FIG. 1, the dispersion medium supply piping 32 looks as if it is connected immediately above the drainage outlet 14. However, the diagram is an overall schematic system diagram, and in actuality, the dispersion medium supply piping 32 is connected to an upper course 13x of the drainage outlet positioned at roughly the same height as that of the drainage outlet 14 opened at the pipe line, which extends almost horizontally to the region positioned at the lowest part of the outward piping 13a. Needless to say, even if the position is not strictly the lowest, the effect of the present invention can be sufficiently effective, and the dispersion medium supply piping 32 can be connected from the vertically lower side or from the horizontal direction.

Figure 4:
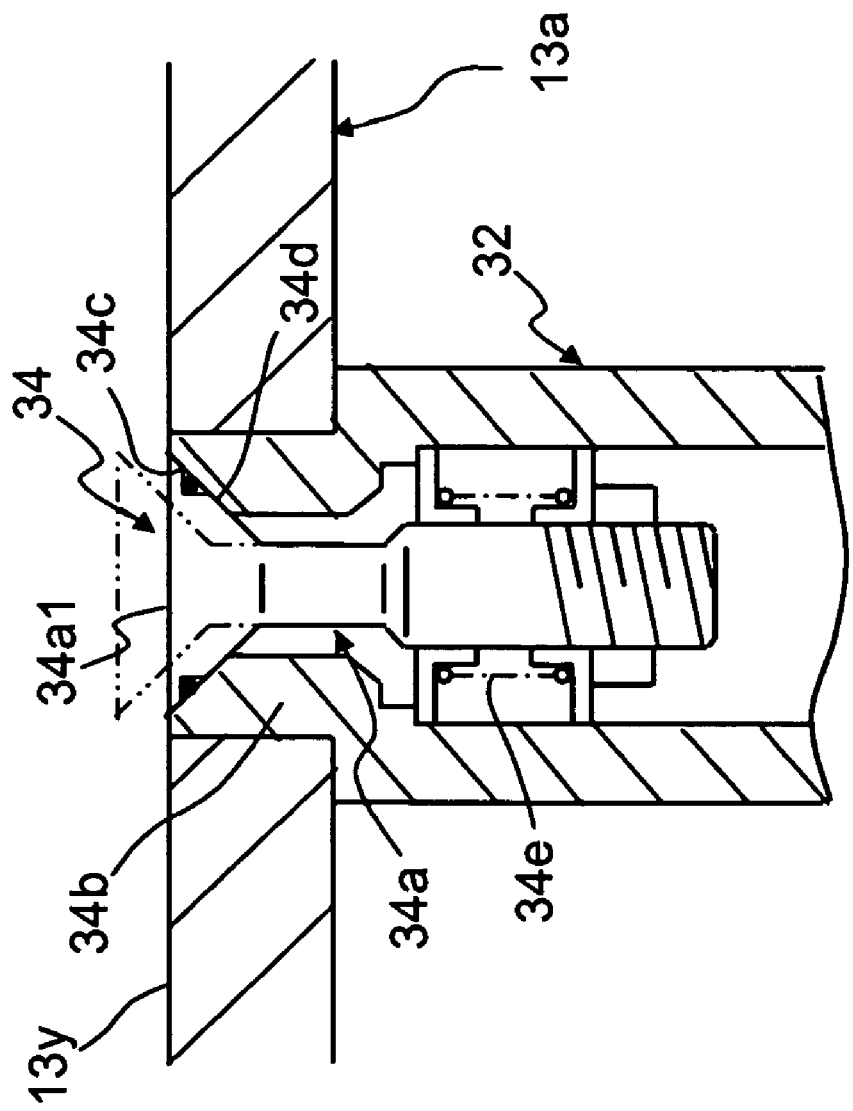
FIG. 4 is a cross-sectional schematic view of a check valve used in the embodiment.

FIG. 4 shows a check valve 34 established in a position where the dispersion medium piping 32 intersects the circulation channel 13. The check valve 34 selectively connects the dispersion medium supply piping 32 to the outward piping 13a of the circulation channel 13 via the opening/closing motion of a valve body 34a, and the valve body 34a is movable forward and backward within a valve housing 34b, and the attachment/detachment of a taper 34d established at the valve body 34a to/from a taper-state sheet 34c established at one end of the valve housing 34b results in the operating/closing motion. The valve body 34a is elastically energized along the direction to seat on the sheet 34c by a spring 34e established between the valve housing 34b and the valve body 34a. The operation of the pour pump 33 causes the upward movement of the valve body 34a resulting in opening the check valve 34, and stopping the pour pump 33 causes the energizing force of the spring 34e and static pressure within the circulation channel 13 resulting in the closure of the check valve 34.

Then, the internal end, in other words, the upper surface 34a1 of the valve body 34a in the closed position, is arranged to be roughly smooth without any unevenness/step relative to a pipe line internal surface 13y of the circulation channel 13.

As mentioned above, in the present embodiment, since the dispersion medium supply system 3 is connected in the vicinity of the drainage outlet 13x positioned at the lowest position of the circulation channel 13 comprising the suspension circulation system 1 so as to pressure pour the dispersion medium 3a from the dispersion medium supply system 3 to the circulation channel 13, air within the circulation channel 13 is forced out. Concurrently, mingling of new air can be avoided, so air ventilation processing basically becomes unnecessary. Consequently, it becomes possible to effectively shorten the time required to the start of measurement. In particular, with this structure, when the pouring speed of the dispersion medium 3a is increased, not only does air mingling not increase, but the effect of forcing out the residual air also becomes high instead, so the time required for pouring itself becomes shorter, and the further reduction of the air residue rate can be accomplished. Associated with this, the generation of unnecessary scattering light can be eliminated, making it possible to effectively improve the S/N ratio of the measured scattered light.

Specifically, the above mentioned drainage outlet 14 is established at the pipe line of the outward piping 13$a$ positioned at the lowest part of the circulation channel 13 and the dispersion medium supply piping 32 is connected to an upper course 13$x$ of the drainage outlet of this pipe line, so maximum forcing out of air can be anticipated.

In particular, since it is constructed so that the dispersion medium supply piping 32 can be selectively connected to the circulation channel 13 of the suspension circulation system 1 via the opening/closing motion of the valve 34, mingling of the circulating particles into the dispersion medium supply piping 32 can be effectively prevented, and the contamination of the dispersion medium 3$a$ and the generation of a dilution error generally can be effectively avoided. Then, the internal end 34$a$1 of the valve 34 at the closed position is arranged to be roughly smooth without any unevenness/step relative to the internal surface of the pipe line in the outward piping 13$a$ comprising the circulation channel 13, so unprepared unevenness where the particles or air may remain will not be formed, and the reduction of measurement accuracy can be avoided.

In the meantime, the present embodiment is also characterized by the point that a multipoint detection type or continuous detection type liquid level sensor 100 is adopted for the liquid level detecting means 10 shown in FIG. 2 so as to intermittently or continuously detect the liquid level within a pre-determined range from the filled level to the shortage level. Then, a detection signal S of the liquid level sensor 100 is entered into the control means or unit 110 to control pouring of the above-mentioned dispersion medium 3$a$ and/or the drainage of the above-mentioned suspension 1$a$ from the control means 110.

The liquid level sensor 100 in the diagram is a float type using a reed relay, and when a float 100$b$ rises along a guide shaft 100$a$, a not-shown terminal established at the float 100$b$ side makes contact with a not-shown multipoint detection terminal or continuous detection terminal established along the axial direction of the guide shaft 100$a$ side, and the liquid level is intermittently or continuously detected. Needless to say, various types can be used for the liquid level sensor, as described later.

Figure 5:
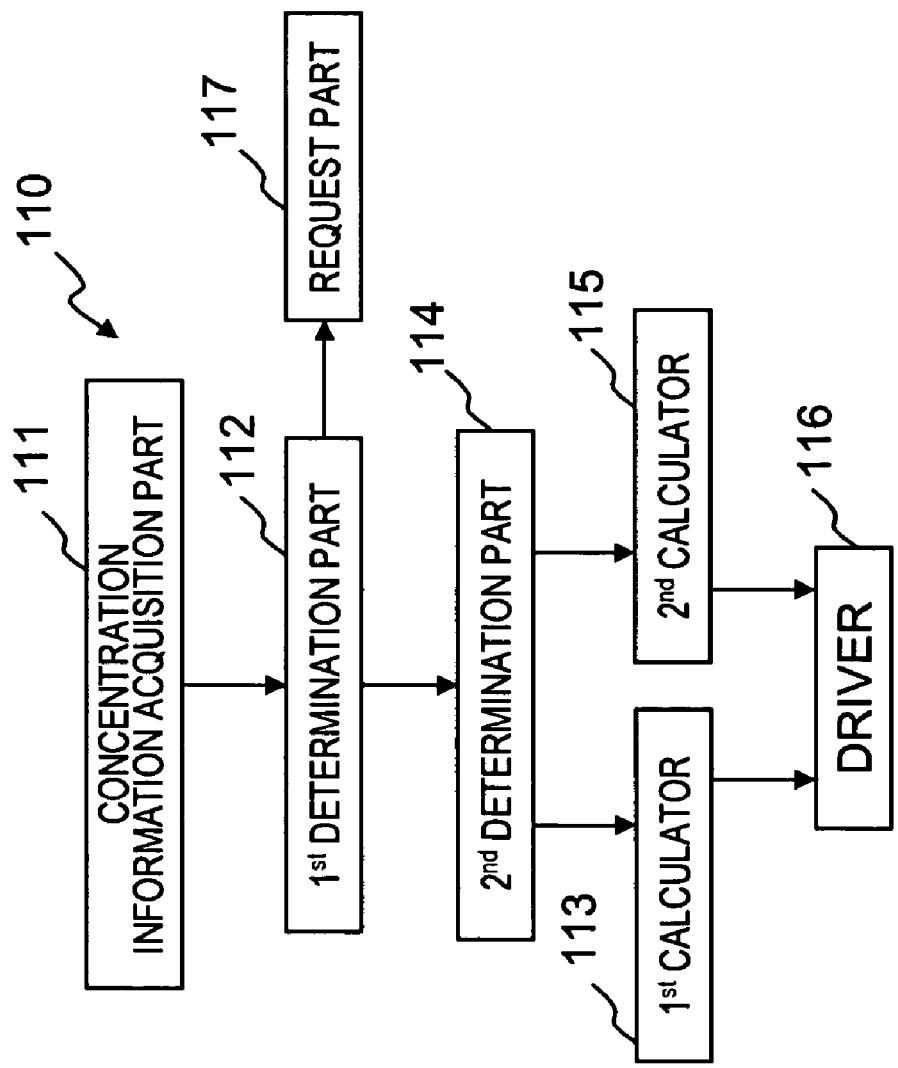
FIG. 5 is a diagram that shows the configuration of the control means in the embodiment.

The above mentioned arithmetic processor 26 serves as the control means 110 in the present embodiment, and the liquid level control program is stored in the memory 26$b$, and the CPU 26$a$ appropriately reads out the program and enters the output signal S from the liquid level sensor 100 via the above-mentioned I/O interface 26$c$, or an operator enters a setting value via the user interface 26$d$, and pre-determined arithmetic processing is performed. Then, as shown in FIG. 5, they collaborate to serve as a concentration information acquisition part 111, a 1st determination part 112, a 1st calculator 113, a 2nd determination part 114, a 2nd calculator 115, a driver 116 and a request part 117.

The concentration information acquisition part 111 acquires the concentration of the particles contained in the suspension 1$a$ from transmittance of the laser beam 2$a$, and includes not only an acquisition means that acquires the information according to the pre-determined operation, but also includes an acquisition means that simply acquires the operational results of the concentration check program. The acquired concentration information does not necessarily have to be a value of concentration itself as in the present embodiment, but is acceptable as long as it is within parameters proportional to the concentration.

The 1st determination part 112 determines whether or not the concentration of the particles contained in the suspension 1$a$ is pre-determined based upon the obtained concentration. The pre-determined concentration is pre-stored as a default value. Needless to say, an operator can provide a setting value.

The 1st calculator 113 calculates the necessary amount of the dispersion medium 3$a$ to be poured if the 1st determination part determines that the concentration is higher. A concentration difference and a necessary amount to be poured according to the difference are pre-stored relative to a numerical expression or a table.

The 2nd determination part 114 determines whether or not the circulation bath 11 is filled due to pouring according to the above-mentioned amount to be poured and the liquid level indicated by the detection signal S of the above-mentioned liquid level sensor 100. A liquid level and a pourable amount to be filled are pre-saved relative to a numerical expression or a table as the occasion demands. The 2nd determination part 114 makes a determination prior to the calculation of the amount to be poured by the above mentioned 1st calculator 113.

The 2nd calculator 115 calculates the necessary amount of the suspension 1$a$ to be drained and of the dispersion medium 3$a$ to be poured to accomplish the pre-determined concentration if the 2nd determination part 114 determines that the circulation bath 11 will be filled by pouring.

The driver 116 drives instruments required for pouring the dispersion medium 3$a$ and/or the drainage of the suspension 1$a$ based upon the calculated value(s) by the above-mentioned 1st calculator 113 and/or 2nd calculator 115. In the present embodiment, as shown in FIG. 2, the pour pump 33 is driven to be ON/OFF for the purpose of pouring the dispersion medium 3$a$, and the directional control valve 17 is driven to be opened/closed to drain the suspension 1$a$. In this case, the driver 116 can directly supervise and control the discharge amount of the pour pump 33 based upon the calculated amount to be poured, or a target liquid level is calculated based upon the amount to be poured, and the driver 116 can also drive ON/OFF to stop the pour pump 33 when the target level is reached based upon the detection signal S of the liquid level sensor 100. If the dispersion medium 3 is preloaded like tap water, an electromagnetic valve is generally used, and is also used for the directional control valve 17 for the drainage of the above-mentioned suspension 1$a$. Even in these cases, the target liquid level is calculated according to the amount to be poured, and it can be designed to control opening/closing to close the valve when the target level is reached based upon the detection signal S from the liquid level sensor 100.

The request part 117 requests the addition of more sample particles x if the above-mentioned 1st determination part 112 determines that the concentration of the suspension 1$a$ is low, and informs an operator of the request in writing or by sound via the user interface 26$d$ as the occasion demands. It is further preferable not only to simply request to add more sample particles x but to request it after calculating the amount to be added.

Figure 6:
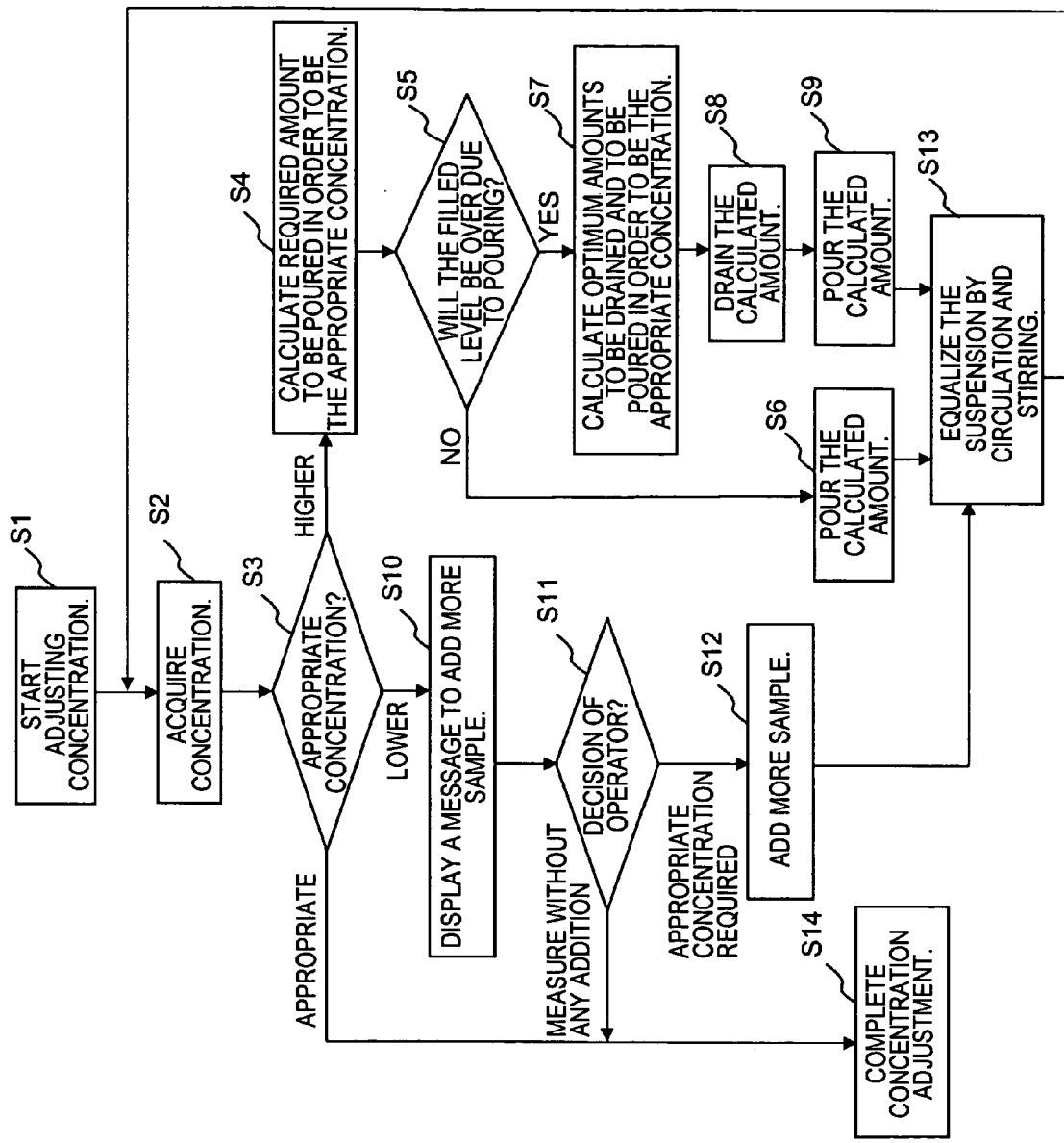
FIG. 6 is a flow chart that shows the procedure for the concentration adjustment implemented in the embodiment.

FIG. 6 is a flow chart that shows the outline of the program executed by control means 110.

When the concentration adjustement is started (S1), first, the concentration is acquired (S2), and a determination is made as to whether or not the acquired concentration is the appropriate concentration (pre-determined concentration) (S3). If the concentration is higher, the required amount of the dispersion medium 3a to be poured in order to be the appropriate concentration is calculated (S4), and a determination is made as to whether or not the circulation bath 11 will overflow if the calculated amount is poured (S5). If it is determined that it will not overflow, the amount to be poured is poured (S6), and if it is determined that it will overflow, an amount of the suspension 1 to be drained and an amount of the dispersion medium 3 to be poured, which are optimum to be the appropriate concentration, are re-calculated (S7). Then, drainage and pouring are performed based upon the calculated amounts (S8 and S9). In the meantime, if it is determined that the concentration is lower in Step S3, the addition of the sample particles x is requested by displaying a message to add more sample (S10), and the addition of sample by the operator (S12) is awaited. However, if the operator enters information to move to measurement without adding any sample, the concentration adjustment process is finished (S14). After the above-mentioned Steps S6, S9 and S12, the suspension 1a is equalized due to the circulation and agitation (S13), respectively, and the operation returns to Step S2 again.

If whether or not the circulation bath 11 will be filled is not considered, the 2nd determination part 114, the 2nd calculator 115 and Steps S5 through S8 are unnecessary.

In the present embodiment, the liquid level detecting means 10 that detects the liquid level of the suspension 1a in the circulation bath 11 at least at multiple points; and the control means 110 that controls pouring the dispersion medium 3a and/or the drainage of the suspension 1a based upon the detection signal S from the liquid level detecting means 10 are established.

In the present embodiment, since the intermediate liquid level can be detected, pouring the dispersion medium 3a and the drainage of the suspension 1a can be more strictly controlled, making it possible to more accurately adjust the liquid level of the circulation bath 11, useful for the concentration adjustment of suspension 1a.

In particular, a liquid level sensor 100, which can detect the liquid level at multiple points or continuously detect the liquid level, is adopted for the liquid level detecting means 10, so the structure can be simplified and made compact, and construction suitable for fine adjustment can be realized.

Further, the control means 110 is constructed to automatically perform a series of controls, including the acquisition of concentration, the determination of concentration, the calculation of amount to be poured, and driving of the pour pump 33 and the directional control valve 17, so the concentration does not have to be adjusted by pouring and/or draining to find the pre-determined one, making it possible to promptly adjust the concentration by dilution and to promptly shift to the measurement of the particle size distribution.

Particularly, even if the circulation bath 11 overflows due to pouring, the control means 110 is designed to pre-determine the overflow and to drain the suspension 1a, and the dilution can be performed avoiding waste as much as possible, so the efficacy of the concentration adjustment can become effective.

In addition, since the control means 110 is designed to request the addition of the sample particles x if it is determined that the concentration is lower, a prompt response by an operator enables an effective response even when the concentration needs to be increased.

Furthermore, the specific construction of each section is not limited to only the above-mentioned embodiment, but it is variously modifiable within the scope of the purpose of the present invention.

Figure 7:
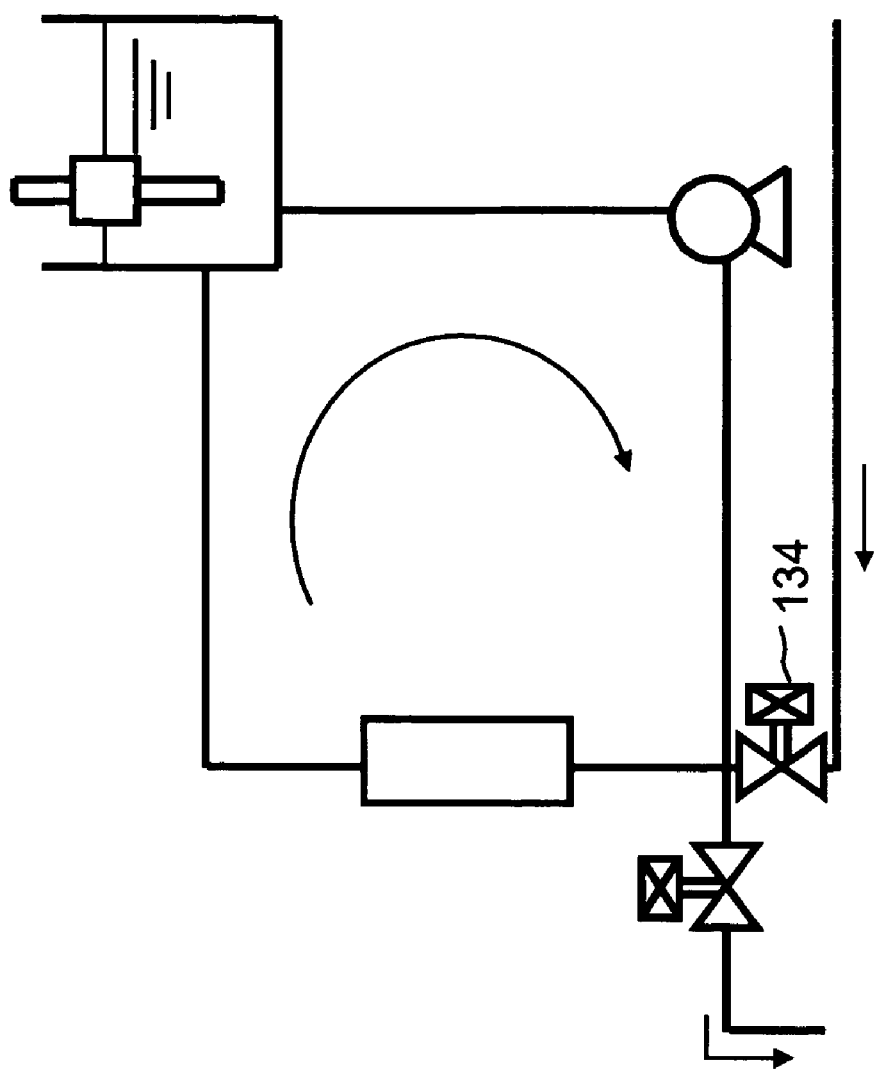
FIG. 7 is a diagram that shows another embodiment of the present invention.

For example, if the dispersion medium 3a is preloaded, as shown in FIG. 7, the arrangement of a switching valve 134 instead of the check valve 34 also enables effective use of tap water as the dispersion medium. Even in this case, the placement of the dispersion medium supply route 3 at the lowest position in the suspension circulation system 1 results in a similar effect to that above.

Figure 8:
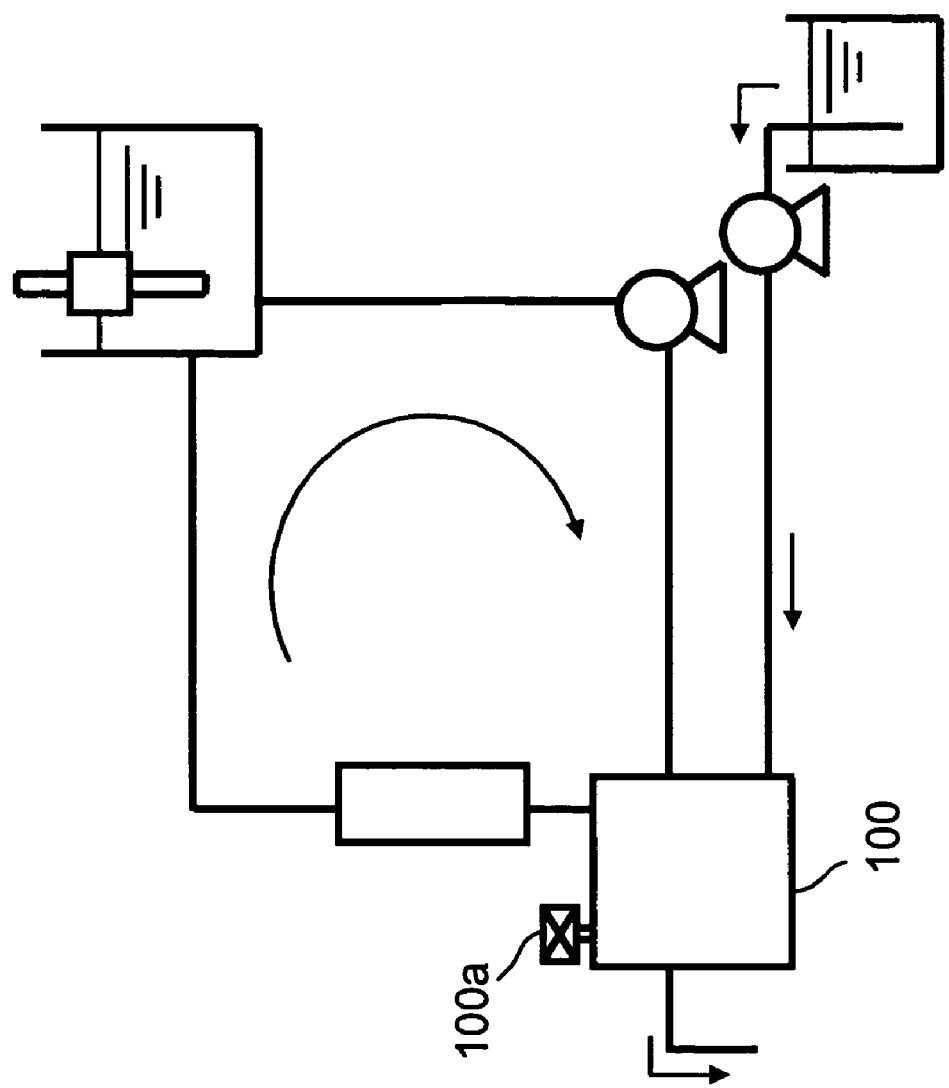
FIG. 8 is a diagram that additionally shows another embodiment of the present invention.

Further, since the suspension drainage system 4 and the dispersion medium pour system 3 gather at positions closer to the suspension circulation system 1, as shown in FIG. 8, it is also effective to form these into a unit by using a single chassis component, assembly piping 100.

This results in the reduction of the air residue as much as possible because a smooth condition without any unevenness or step at the connection section can be obtained. Concurrently, another effect of the decrease of dead volume, structure simplification and cost reduction due to the reduction of number of the components can be obtained. Symbol 100a is a drainage actuator to control the drainage of a suspension. Even in this case, concerning the assembly piping 100, the placement of the dispersion medium supply route 3 at the lowest position in the suspension circulation system 1 results in an effect similar to that mentioned above.

Figure 9:
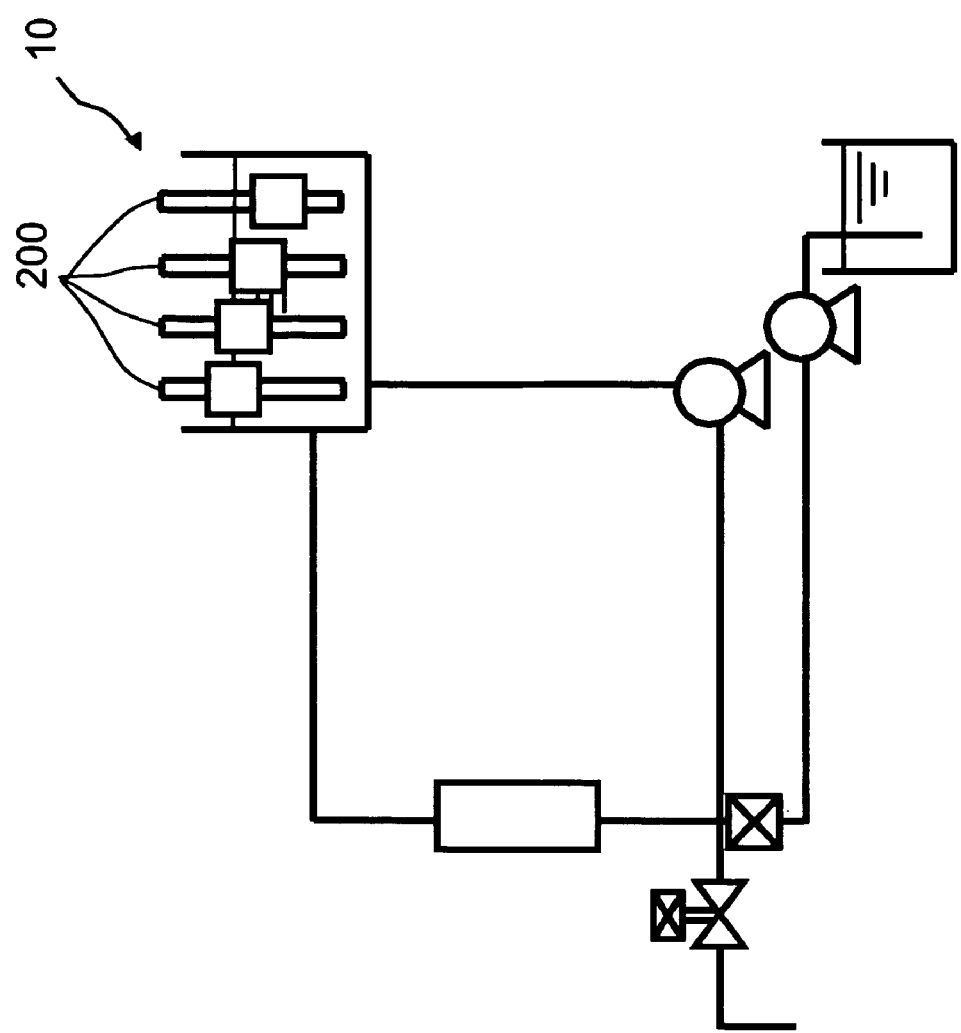
FIG. 9 is a diagram that additionally shows another embodiment of the present invention.
Figure 10:
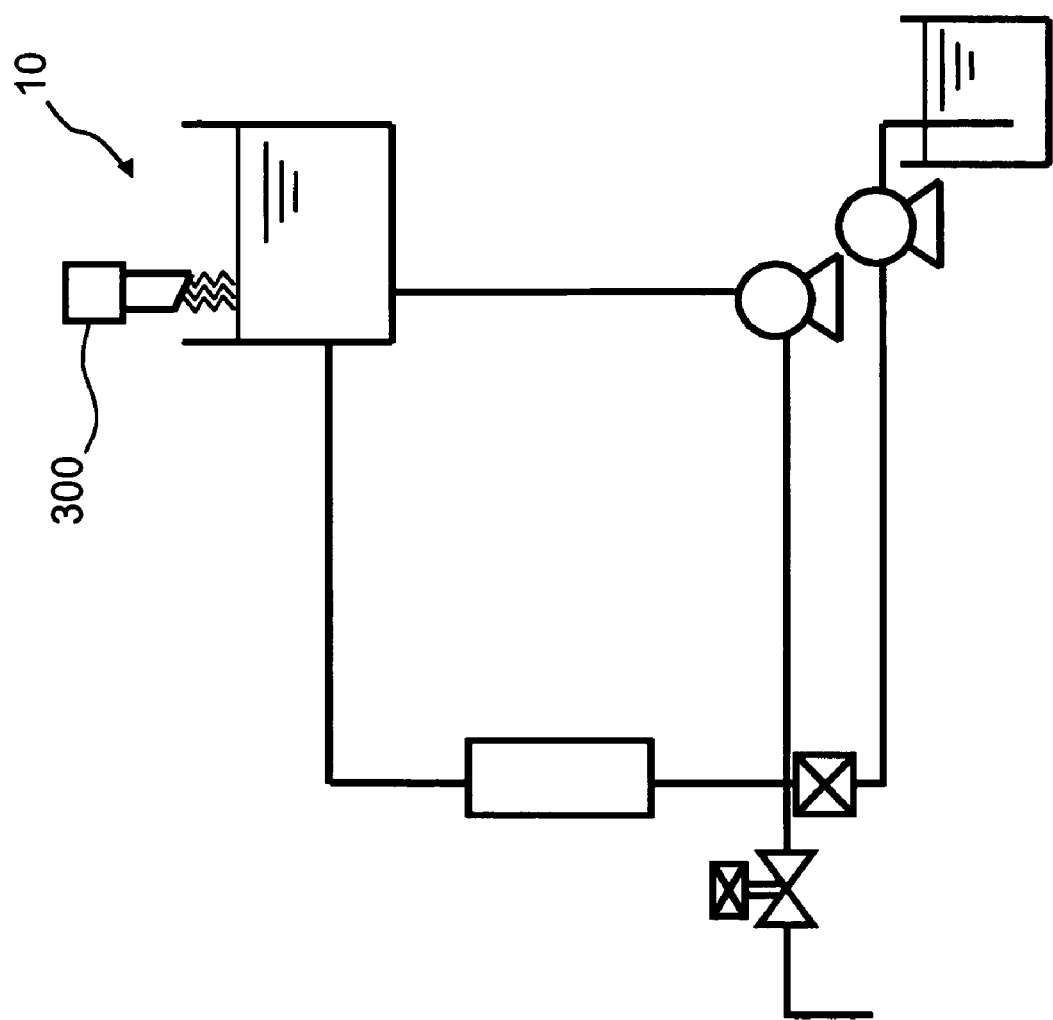
FIG. 10 is a diagram that additionally shows another embodiment of the present invention.

In addition, using multiple liquid level sensors 200 for the liquid level detecting means 10, as shown in FIG. 9 enables configuration at low cost, or, as shown in FIG. 10, using a non-contact sensor 300, such as an optical type by utilizing the difference of light reflectivity or the difference of a refraction angle, a conductive type, an electrostatic capacity type or an ultrasound type, enables effective avoidance of the obstruction of stirring because it will not be physically immersed into circulation bath 11.

What is claimed is:

1. A particle size distribution measurement device comprising;
    a suspension circulation system where a circulation bath and a flow cell are connected via a circulation channel so as to circulate a suspension where particles are dispersed in a dispersion medium;
    an optical measurement system where an inspection light is irradiated onto the suspension flowing within the flow cell, and a particle diameter distribution of the particles in the suspension is measured based upon diffracted and/or scattered light;
    a dispersion medium supply system that supplies the dispersion medium to the suspension circulation system; and
    a suspension drainage system that drains the suspension from a drainage outlet established in the circulation channel,
    and wherein the dispersion medium supply system is connected in the vicinity of the drainage outlet of the circulations channel composing the suspension circulation system so as to pressure-pour the dispersion medium from the dispersion medium supply system to the circulation channel.

2. The particle size distribution measurement device according to claim 1, wherein, the drainage outlet is established at a pipe line positioned at the lowest part of the circulation channel, and the dispersion medium supply system is connected to an upper course of the drainage outlet of the pipe line.

3. The particle size distribution measurement device according to claim 1, designed such that the dispersion medium supply can be selectively connected to the suspension circulation system via the opening/closing motion of a valve body, and an internal end of the valve body situated at the closed position is arranged to be roughly smooth without any unevenness/step relative to the internal surface of the pipe line of the circulation channel.

4. The particle size distribution measurement device according to claim 1, wherein, assembly is accomplished of the suspension drainage system, the suspension supply system and the circulation channel as a unit using a single chassis component.

5. The particle size distribution measurement device of claim 1 further including a check valve connecting the dispersion medium supply system to the circulation channel.

6. The particle size distribution measurement device of claim 5 wherein the check valve includes a valve body with an exterior surface complementarily to an internal surface of the circulation channel when closed to provide a smooth flow path.

7. The particle size distribution measurement device of claim 6 wherein the valve body has an annular tapered shape extending from the exterior surface for seating the valve body when closed.

8. The particle size distribution measurement device of claim 1 wherein the circulation bath is mounted above the dispersion medium supply system and includes a circulation pump connected to the circulation channel and an ultrasound oscillator to mix the particles in the circulation chamber downstream of the suspension drainage system.

9. The particle size distribution measurement device of claim 1 further including a control unit, a signal processor, and a liquid level sensor, wherein the liquid level sensor detects a fill level of the circulation bath and the control unit activates the signal processor for measuring particles when the fill level reaches a predetermined level.

10. The particle size distribution measurement device according to claim 9 wherein, the control unit includes,
  a concentration information acquisition part that acquires information concerning the concentration of particles contained in the suspension according to transmittance generally of the inspection light;
  a first determination part that determines whether or not the concentration of the particles contained in the suspension is the pre-determined concentration based upon the acquired concentration information;
  a first calculator part that calculates the required amount of the dispersion medium to be poured if the first determination part determines that the concentration is higher; and
  a driver unit that drives the dispersion medium supply system for pouring the dispersion medium based upon a value calculated by the first calculator part.

11. The particle size distribution measurement device according to claim 10 wherein, the control unit includes with a request part that requests an addition of more particles if the first determination part determines that the concentration of particles is low.

12. The particle size distribution measurement device according to claim 9 wherein, the control includes,
  a concentration information acquisition part that acquires information concerning the concentration of particles contained in the suspension according to transmittance generally of the inspection light;
  a first determination part that determines whether or not the concentration of the particles contained in the suspension is a pre-determined concentration based upon the acquired concentration information;
  a first calculator part that calculates the required amount of the dispersion medium to be poured if the first determination part determines that the concentration of particles is higher;
  a second determination part that determines whether or not the circulation bath is filled based on the liquid level detected by the liquid level sensor;
  a second calculator part that calculates a required amount of the suspension to be drained and a required amount if the dispersion medium to be poured when determining that the circulation bath is to be filled, and a driver unit that drives the dispersion medium supply system to control the dispersion medium based upon a value calculated by the first calculator part and/or the second calculator part.

13. A particle size distribution measurement device comprising;
  a suspension circulation system where a circulation bath and a flow cell are connected via a circulation channel to circulate a suspension where particles are dispersed in a dispersion medium;
  an optical measurement system where inspection light is irradiated onto the suspension flowing within the flow cell, and the particle size distribution of the particles in the suspension is measured based upon diffracted light and/or scattered light;
  a dispersion medium supply system that supplies the dispersion medium to the suspension circulation system;
  a suspension drainage system that drains the suspension from a drainage outlet established in the circulation channel, and wherein the dispersion medium supply system is constructed to be connected in the vicinity of the drainage outlet of the circulation channel composing the suspension circulation system so as to pressure-pour the dispersion medium from the dispersion medium supply system to the circulation channel;
  a drainage outlet is established including a pipe line positioned at the lowest part of the circulation channel and the dispersion medium supply system is connected to an upper course of the drainage outlet of the pipe line; and
  a valve body, the dispersion medium supply system can be selectively connected to the suspension circulation system via the opening/closing motion of the valve body, with the internal end of the valve body at the closed position being arranged to be roughly smooth without any unevenness/step relative to the internal surface of the pipe line of the circulation channel.

* * * * *